United States Patent [19]

Vignery

[11] Patent Number: 5,858,978
[45] Date of Patent: *Jan. 12, 1999

[54] PHARMACEUTICAL COMPOSITIONS CONTAINING CALCITONIN GENE-RELATED PEPTIDE (CGRP) AND USE THEREOF TO AMELIORATE HYPERIMMUNE MEDIATED DISEASES AND ABNORMAL CONDITIONS

[75] Inventor: Agnès Marie-Claude Vignery, New Haven, Conn.

[73] Assignee: Yale University, New Haven, Conn.

[ * ] Notice: The term of this patent shall not extend beyond the expiration date of Pat. No. 5,635,478.

[21] Appl. No.: 837,114

[22] Filed: Apr. 14, 1997

Related U.S. Application Data

[63] Continuation of Ser. No. 125,275, Sep. 23, 1993, Pat. No. 5,635,478, which is a continuation of Ser. No. 408,573, Sep. 18, 1989, abandoned.

[51] Int. Cl.$^6$ .............................. A61K 38/00; C07K 5/00; C07K 7/00
[52] U.S. Cl. .............................................. 514/12; 530/324
[58] Field of Search ................................. 514/12; 530/324

[56] References Cited

U.S. PATENT DOCUMENTS 5,635,478  6/1997  Vignery ..................................... 514/12

OTHER PUBLICATIONS

Nong et al., *Journal of Immunology*, vol. 143, pp. 45–49, No. 1, Jul. 1, 1989.
Asahina et al., *Proc. Natl. Acad. Sci. USA*, vol. 92, pp. 8323–8327, Aug. 1995.
Asahina et al., *Journal of Immunology*, Inhibition of Induction of Hypersensitivity by CGRP, Dec. 94, pp. 3056–3061.
Palluault et al., "Targeted Expression of Calcitonin Gene Related Peptide to Beta Cells of NOD Mice Prevents Insulin–Dependent Diabetes Mellitus", Yale University, Abs S518, 1995.

*Primary Examiner*—Avis M. Davenport
*Attorney, Agent, or Firm*—Millen, White, Zelano & Branigan, P.C.

[57] ABSTRACT

Calcitonin gene-related peptide and calcitonin regulate immune cell function and cytokine release and are useful in the treatment of immune cell and cytokine mediated, immune mediated diseases, such as rheumatoid arthritis, treating viral infections, tumors and organ transplants.

7 Claims, No Drawings

PHARMACEUTICAL COMPOSITIONS CONTAINING CALCITONIN GENE-RELATED PEPTIDE (CGRP) AND USE THEREOF TO AMELIORATE HYPERIMMUNE MEDIATED DISEASES AND ABNORMAL CONDITIONS

This is a continuation, of the application Ser. No. 08/125,275 filed Sep. 23, 1993 now U.S. Pat. No. 5,635,478 which is a continuation of Ser. No. 07/408,573, filed Sep. 18, 1989, now abandoned.

This invention relates to a me immune response with calcitonin (CT) and with calcitonin gene-related peptide (CGRP) and to the treatment of various diseases and abnormal conditions associated with the immune response.

BACKGROUND OF THE INVENTION

Macrophages and lymphocytes play a central role in inflammatory reactions in response to foreign or infectious agents. Monocytes are first chemotactically attracted to the injured tissue in which they differentiate structurally and functionally into tissue specific macrophages. Via the expression of specific receptors and the release of appropriate cytokines, macrophages govern and coordinate in a well ordered series of cellular mediated events the inflammatory reaction which eventually leads to the eradication of the intruder and the repair of the damaged tissue. When inflammation persists and becomes chronic, macrophages that have been accumulating fuse to form multinucleated giant cells onto the foreign substrate Although these giant macrophages appear to be actively involved in tumor defense mechanisms and bone resorption (where they are called osteoclasts), the functional relevance of their multinucleation remains highly speculative. Earlier reports indicate that giant cells can phagocytose as effectively as macrophages through a variety of receptors. This suggests that macrophages and giant cells share functional components and are equally capable of participating in host defense mechanisms. It has previously been shown that giant cells, whether elicited in vivo or in vitro are, like osteoclasts, polarized and express antigens that are not detected in mononucleated macrophages. To further investigate the role played by giant cells in chronic inflammatory reactions and to elucidate the putative interactions between giant cells and/or osteoclasts and the surrounding immune and nonimmune cells, the level of release of two cytokines, IL-1 and IL-6, by macrophages was compared to that of multinucleated giant cells. Because osteoclast activity is strongly inhibited by CT, the effect of this hormone was investigated to determine whether it could alter the level of release of these cytokines by multinucleated macrophages. This investigation demonstrated that giant cells, like peritoneal macrophages, do release spontaneously detectable levels of both IL-1 and IL-6; that CT is a weak inhibitor of IL-1 release but is specific for giant cells; that CGRP, a neuropeptide encoded by the same gene as CT, specifically blocks the release of IL-1 in both peritoneal macrophages and multinucleated giant cells; and that this inhibitory action of CGRP is mediated by intracellular cyclic adenosine monophosphate (cAMP) dependent mechanism. This work also demonstrates that CGRP directly alters the pattern of cytokine release by lymphocytes and has a profound effect on cytokine releasing cells (keratinocytes, mesangial cells, glial cells, etc.).

In a recently published paper, Nong, Yu-Hua et al., J. Immun., 143, 45–49, No. 1, pp. 45–49 (Jul. 1, 1989), report that CGRP profoundly inhibit the ability of macrophages to produce $H_2O_2$ in response to IFN or to act as APC and that CT also prevented macrophage activation, suggesting to the authors that CGRP and CT play an important role in modulating the ability of macrophages to present Ag and to respond to activating factors.

SUMMARY OF THE INVENTION

In a method aspect, this invention relates to a method of regulating the function of macrophages and lymphocytes releasing cells, respectively, in a living mammal which comprises administering thereto an immune cell function-inhibiting amount of CGRP.

In another method aspect, this invention relates to a method of regulating the rate of cytokine release from giant cells in a living mammal which comprises administering thereto an IL-1 or IL-1 and IL-2, respectively release-inhibiting amount of CT.

In a preferred aspect, this invention relates to a method of treating an immune response-associated disease or immune response-mediated abnormal condition in an animal by the administration thereto of an amount of CGRP effective to ameliorate the disease or abnormal condition.

In another preferred aspect, this invention relates to a method of treating an immune response-associated disease or immune response-mediated abnormal condition in an animal by the administration thereto of an amount of CT effective to ameliorate the disease or abnormal condition.

In another method aspect, this invention relates to a method for the symptomatic treatment of a disease resulting from a viral infection in an animal which comprises administering systemically to the infected animal successive therapeutically effective doses of CGRP or CT.

In a composition aspect, this invention relates to a pharmaceutical composition adapted for noningestion systemic administration thereof comprising an immune cell function-inhibiting amount per unit dosage of CGRP in admixture with a pharmaceutical carrier adapted for noningestion systemic administration.

DETAILED DISCUSSION

CGRP and CT are known commercially available peptides.

Eel calcitonin has the formula

Human calcitonin has the formula

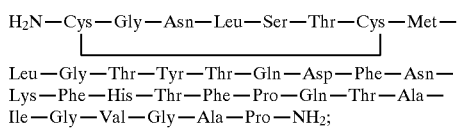

Salmon 1 calcitonin has the formula

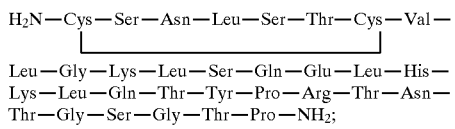

Human CGRP has the formula

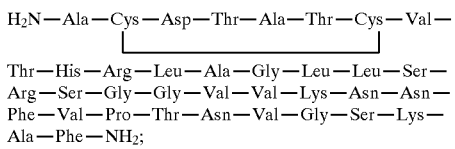

Rat CGRP has the formula

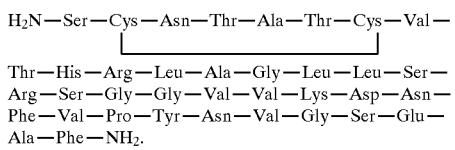

It can be seen from the above formulae that all 5 of the above species have a beginning and ending -NH$_2$ group; a ring proximate (at or penultimate to) one end of the molecule; which ring has 6 (CGRP) or 7 (CT) ring members with two Cys and a Thr as adjacent ring aminoacid (AA) members. The CT species all have 37 AA groups and a ring member Cys and a Pro as its terminal AA groups and the CGRP species all have 32 AA groups and a ring member Cys and a Phe AA as its penultimate and terminal AA groups, respectively.

In accordance with this invention, it has been demonstrated that the neuropeptide CGRP is a potent inhibitor of cytokine release by peritoneal and multinucleated macrophages and lymphocytes and that CT alters giant cells' immune function. It appears that this inhibiting effect is mediated by cAMP. It has also been demonstrated that 1,25(OH)$_2$-vitamin D$_3$ specifically stimulates IL-1 release by peritoneal macrophages, but not by giant cells. Finally, the research results described herein show that both macrophage populations release (constitutively) interleukin-6 and that neither CGRP nor 1,25(OH)$_2$-vitamin D$_3$ appear to significantly alter this process.

While most investigations on the immunological role of macrophages have employed powerful agents such as LPS to activate these cells, in the present investigation, a specific attempt was made to minimize macrophage activation to reproduce in vitro the chronic stage of the inflammatory reaction as well as the in situ tissue environment of resident peritoneal macrophages. This enabled the generation of giant cells, as in chronic inflammatory sites, where macrophages are dense and either surround the foreign substrate, or as so-called osteoclasts resorb bone. Although both in vitro and in vivo elicited multinucleated macrophages share with osteoclasts a rich and polarized concentration of Na,K-ATPase and of a lysosomal membrane antigen, it was not clear whether macrophage multinucleation reflected a true differentiation process or was a dead end for exhausted macrophages. By measuring the amount of cytokine release and its putative regulation by cytokines and hormones that affect osteoclast function, one could potentially estimate the functional relevance of multinucleation.

The investigative route which was taken to verify that in vitro elicited giant cells would respond, as osteoclasts do, to calcitonin, led to testing the effects of CGRP and consequently discovering that this neuropeptide may directly control inflammatory reactions via cytokine release by macrophages and lymphocytes. Interactions between neurological, endocrine and immune systems have been reported before. Substance P, substance K and the carboxyl-terminal peptide SP(4–11) have recently been shown to stimulated IL-1 and IL-6 release by human blood monocytes. However, this is the first report of a neuropeptide controlling the immune reaction at its early and critical stage by blocking specifically cytokine secretion and immune response. Cytokines are very potent with diverse biological activities which affect nearly every organ when administered in vivo. Inasmuch as IL-1, for instance, has beneficial effects on host defense mechanisms, its activities are also associated with pathogenic disease processes such as arthritis and diabetes. Therefore, the use of an inhibitor of IL-1 or IL-2 production provides a new method for ameliorating the symptoms of and altering the course of such diseases. The present study produced evidence that CGRP induces an accumulation of cAMP and that forskolin mimics the biological effects in a T cell assay, therefore confirming that cAMP mediates the inhibition of T cell proliferation via IL-1 secretion. CGRP may be secreted by local nerve endings which remain in control of the chronic phase of the reaction and therefore oversee the evolution and progression of the entire inflammatory reaction. In accordance with this hypothesis, CGRP is involved in chronic inflammatory reactions such as, for instance, rheumatoid arthritis.

By responding to calcitonin but not to 1,25(OH)$_2$-vitamin D$_3$, giant cells appear to be differentially regulated from macrophages, which suggests that they may play a novel immunological role during with chronic inflammation. The close relationship between giant cells and osteoclasts further suggests that the stimulatory effect of 1,25(OH)$_2$-vitamin D$_3$ on bone resorption in vitro may be mediated by local cells such as macrophages which respond to this hormone.

The reason why calcitonin receptor expression appears to be restricted to multinucleated macrophages is not known. One possible explanation is that multinucleation alters the CGRP receptor post-translationally and permits calcitonin binding and activity. Another possibility is that multinucleation modifies CGRP gene expression, generating a different receptor by alternative splicing of the mRNA. A third possibility is that multinucleation activates the expression of a different gene coding for the CT receptor. A number of alternative mechanisms can be suggested involving trans- or cis-splicing of gene transcripts leading to the expression of one or two receptors sharing high sequence homology.

From this study, it appears that giant cells share with osteoclasts, beyond their origin (i.e., fusion of mononuclear phagocytes), their high expression of Na,K-ATPases and their ruffled plasma membrane enriched in a 100 kd lysosomal membrane antigen (Citation?), the expression of receptors for calcitonin. This receptor expression appears to be associated with multinucleation. Thus, giant cells may differ from osteoclasts by the substrate onto which they differentiate and one can hypothesize that bone remodeling mimics a chronic inflammatory reaction.

Taken together, the results reported herein show that unstimulated mono- and multinucleated macrophages release detectable levels of IL-1 and that their accumulation of intracellular cAMP, whether mediated by forskolin of CGRP, inhibits this release. This suggests that regardless of their degree of activation, IL-1 secretion by macrophages is strongly inhibited by activators of adenylate cyclase.

Importantly, 1,25(OH)$_2$ vitamin D$_3$, a potent activator of osteoclastic bone resorption, specifically stimulates IL-1 release by peritoneal macrophages while giant cells fail to respond.

CGRP and CT are useful in the treatment of a variety of ailments and diseases in animals, particularly those which result in inflammatory and related stress conditions manifesting themselves in the afflicted animal. For example, CGRP and CT are useful in relieving the pain, tenderness, fever and dysfunction following acute traumatic injuries, surgery and in the treatment of orthopedic dysfunction, e-g., bony exostosis. CGRP also is effective in treating viral diseases, e.g., human influenza A and B, viral horse pneumorhinitis, canine distemper, picorna virus induced feline pneumotracheitis, dysfunctions based on the family of herpes virus and diseases associated with H.I.S. CGRP and CT are useful in the treatment of a variety of acute and chronic inflammatory conditions. Its anti-inflammatory activity is manifested in various animal models of induced inflammation, viz., foot paw edema in the rat produced by carrageenin, yeast or silver nitrate; adjuvant-induced polyarthritis in the rat; passive cutaneous arthritis reaction; cotton pellet granuloma in the nonadrenalectomized and bilaterally adrenalectomized rat; pox virus-induced skin edema in the rabbit; PVA sponge implant-induced inflammation and wound healing and antiserum-induced skin edema and active anaphylaxis in the guinea pig and the mouse.

Among the inflammatory conditions for which CT and CGRP are useful in the treatment thereof, are those in which synthetic anti-inflammatory agents have limited utility, e.g., because of toxic side effects upon prolonged use.

More specifically, CT and CGRP are useful in ameliorating inflammatory conditions and mitigating the effects thereof, for instance those involving the urinary tract and the joints, in various mammals. It is useful in alleviating the symptoms of and the structural deformities associated with post-traumatic arthritis and rheumatoid diseases, such as bursitis, tendonitis, osteoarthritis, nonsurgical disc syndrome and myositis.

CGRP and CT are also useful in the treatment of diseases involving an imbalance of the auto-immune system, alone and in combination with drugs conventionally used to treat such diseases. Typical are the "collagen" type diseases, e.g., rheumatoid arthritis, lupus erythematosus and scleroderma, allergic states, e.g., penicillin reaction, which are characterized by multiple wheals, indurations, erythemas, edema or itching, and drug-induced photosensitization.

In addition to its anti-inflammatory effects, CGRP and CT protect from shock reactions produced upon antigenic challenge after prior sensitization.

CGRP and CT can be used in conjunction with accepted forms of therapy and medication, e.g., hormonal, including androgen and estrogen, therapy.

CGRP and CT also can be used concurrently or alternatingly with steroids in anti-inflammatory therapy, e.g., with cortisone, hydrocortisone, prednisone, prednisolone, and the corresponding $\Delta^{1,4}$-9α-fluoro-16-hydroxy, 16α-methyl and 16β-methyl substituted ster e.g., dexamethasone, fluorocortisone, fluoromethalone, methylprednisolone, triamcinolone and its acetonide, betamethasone, and their known esters and derivatives, and nonsteroid anti-inflammatory agents, e.g., acetylsalicylic acid, salicylamide, aminopyrine, chloroquine, hydroxychloroquine, phenylbutazone and indomethacin. CGRP and CT can also be used concurrently or alternatingly with known agents used in antibacterial and in anti-viral therapy to increase the effectiveness of conventional dosages of the known agents or, by reducing such dosages of such agents, the toxic and side effects ordinarily associated with such therapy.

The pharmaceutical compositions of this invention comprise CGRP and/or CT and a pharmaceutically acceptable carrier. The form and character which this carrier takes is, of course, dictated by the mode of administration.

Oral administration, e.g., sublingual, is possible, particularly if the peptide is protected from the destructive action of the acid pH and enzymes of the stomach, e.g., in the form of an enteric coated tablet, although much larger doses are generally required by this route. CGRP has topical activity, e.g., when applied as a solution, aerosol, cream, ointment, salve, etc., which renders it useful for treating corneal and conjunctival, respiratory, genito-urinary and dermatological disorders. Desirably, it is administered with a surfactant and/or penetrant to ensure better contact and penetration.

The pharmaceutical compositions can, e.g., be in a form of pills, dragees and tablets, provided they are coated by known techniques to delay disintegration and absorption in the gastro-intestinal tract and to protect the CGRP or CT from stomach acid and enzymes.

Aqueous solutions contain CGRP or CT in admixture with excipients suitable for the manufacture of stable aqueous solutions, e.g., NaCl, to provide a saline or isotonic solution, buffer agents, acids or bases, etc. The aqueous solution can also contain one or more preservatives, for example, ethyl or n-propyl p-hydroxybenzoate.

Storage-stable compositions can be produced in accordance with the methods of U.S. Pat. No. 3,637,640 and the prior art cited therein, whose disclosures are incorporated herein by reference.

Oily suspensions may be formulated by suspending CGRP or CT in an oil suitable for injection or topical administration, in a vegetable oil, e.g., arachis oil, olive oil, sesame oil or coconut oil, or in a mineral oil, e.g., a liquid paraffin. The oily suspensions may contain a thickening agent, for example beeswax, hard paraffin or cetyl alcohol. These compositions may be preserved by the addition of an antioxidant, e.g., ascorbic acid.

The pharmaceutical compositions of the invention can be in the form of oil-in-water emulsions suitable for parenteral administration. The oily phase may be a vegetable oil, e.g., olive oil or arachis oils, or a mineral oil, e.g., liquid paraffin or mixtures of these. Suitable emulsifying agents are naturally occurring gums, e.g., gum acacia or gum tragacanth, naturally occurring phosphatides, e.g., soya bean lecithin and esters of partial esters derived from fatty acids and hexitol anhydrides, for example, sorbitan monooleate, and condensation products of the said partial esters which ethylene oxide, for example, polyoxy-ethylene sorbitan monooleate.

The compositions of this invention can also be in the form of an aerosol for inhalation or topical administration or slow-dissolving pellets for implantation.

The compositions of this invention can be administered parenterally or topically. The term parenteral as used herein includes subcutaneous, intradermal, intravenous, intramuscular, intraocular, intrastromal, intrasynovial, intrathecal, intramural, intraarticular, intraperitoneal, intrascrotal, intraosseous, intraspinal, intraligamentous and intrasternal. Intramuscular, and subcutaneous administration is usually preferred except when the CGRP or CT is administered proximate a localized area of inflammation.

The pharmaceutical compositions can be in the form of a sterile injectable preparation, for example, as a sterile injectable aqueous solution. The solution can be formulated according to the known art using those carriers mentioned above. The sterile injectable preparation can also be a sterile injectable solution or suspension in a nontoxic parenterally acceptable diluent or solvent, e.g., 1,3-butanediol.

The compositions of this invention can be in the form of suppositories for vaginal and rectal administration. These compositions can be prepared by mixing CGRP or CT with a suitable nonirritating excipient which is solid at ordinary temperatures but liquid at body temperature and will therefore melt in the rectum or vagina to release the drug, e.g., cocoa butter and polyethylene glycols.

The compositions of this invention combine an effective unit dosage amount of CGRP and/or CT, i.e., either is present at a concentration effective to evoke the desired response when a unit dose of the composition is administered by the route appropriate for the particular pharmaceutical carrier. For example, liquid compositions, both topical and injectable, usually contain about 0.5 to 100 mg of the peptide per 0.25 to 10 cc, preferably about 0.5 to 5 cc, except I.V. infusion solutions, which can also be more dilute, e.g., 0.5 to 20 mg of the peptide per 50–1,000 ml, preferably 100–500 ml of infusion solution. Tablets, capsules and suppositories usually contain 1.0 to 500 mg, preferably 10 to 100 mg, per unit dosage.

The weight ratio of CGRP or CT to liquified propellant in an aerosol for topical or inhalation administration can be quite high, e.g., 0.5–5%. Topical compositions usually contain one of the-peptides in a concentration of 0.1–1% in aqueous solution or nonaqueous suspension.

The amount of either peptide administered is dependent on several factors, including the species of patient, the condition of the patient prior to the peptide therapy, the particular disease and its progression and the route of administration. The usual individual parenteral dose range of the peptide is about 10 mg to 100 mg, usually 25 mg to 75 mg. The size of an individual dose is primarily dependent upon the dynamics of the disease pattern. For instance, in an acute stage of a disease, e.g., with associated toxemia or uremia, injections spaced about every 6 hours may be required, with the frequency subsequently reduced to 8–12 hours and then every 24 hours or longer, depending on the clinical picture. Thus, during the acute state of a disease, the frequency of the injections is often more critical than the amount of each individual dose.

Larger individual doses are usually administered when the peptide is administered orally, e.g., 5 mg, 25, 50 or 100 mg, or even more. Similarly, when a solution or suspension of the peptide is applied topically to the skin or infused into the bladder, vagina, large intestine, etc., the total amount of peptide administered in single uninterrupted dose can vary from 5 to 100 mg or more. Conversely, when the peptide is administered into the respiratory tract, e.g., in the treatment of asthma, anaphylactic or other acute shock conditions, e.g., as a spray, mist, aerosol, etc., lesser amounts, e.g., 0.5 to 25 mg or less may be indicated.

The spacing of the individual doses is also partially determined by the nature of the ailment. In treatment of inflammatory syndromes, the selected peptide is usually administered in multiple successive dosages, spaced as frequently as 6–12 hours apart and as long as six weeks apart. Usually, daily doses are administered until symptomatic relief, e.g., from pair and stiffness, is obtained. Thereafter, doses are spaced further apart, the frequency being adjusted so that recurrence of symptoms is avoided and relief maintained. Treatment can be continued over a period of several weeks or months, and indefinitely for advanced chronic cases.

In treating viral infections, the selected peptide is initially administered in multiple successive dosages usually spaced every 12 to as frequently as every 4 hours.

CGRP and CT are usually administered by instillation or by injection, e.g., intramuscularly, subcutaneously, intravenously or intradermally. I.M. is preferred, except in acute situations, where I.V. is sometimes preferred for more rapid onset of effect, and in certain localized disorders where local injection may be more effective. Individual doses usually fail within the range of 10–100 mg. The preferred dosage for humans is about 50 mg. The exact dosage is not critical and depends on the type and the severity of the disease.

Contemplated equivalents of this invention are methods and compositions wherein the CGRP is replaced by a structurally related peptide which possesses the aminoacid spacial configuration of CGRP which is responsible for its IL-1 release inhibiting activity, which configuration can be determined by conventional structure-activity peptide analysis.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications cited herein are hereby incorporated by reference.

MATERIAL AND METHODS

Cells

Rat alveolar and peritoneal macrophages were obtained from 12 week old Fisher 344 rats (Charles River, Kingston, N.Y.). Alveolar macrophages were collected by tracheobronchial lavage as previously described (Vignery et al., J. Histochem Cytochem., 1989). Peritoneal macrophages were collected from the same rats prior to the lung lavage. The collected cells were: (i) washed twice in Minimum Essential Medium with Earle's salts (MEME) supplemented with 2 mM L-glutamine and vitamins; (ii) plated in 6 well dishes at $10^7$ cells/ml, $10^6$ cells per well, in MEME containing 10% heat inactivated human serum (HS); (iii) incubated for 20 minutes at 37° C. in 5% $CO_2$, 95% air to let the macrophages adhere; (iv) subsequently grown at $10^6$ cells/ml of MEME containing 5% heat inactivated HS. Cells were cultured in FCS for the IL-6 bioassay. All tissue culture reagents were purchased from Gibco Laboratories, Grand Island, N.Y. The adherent cell populations were composed of 99% macrophages and a few occasional polymorphonuclear cells as determined by Wright stain.

Interleukin-1 and Interleukin-6 Release Macrophage supernatants

To estimate the release of IL-1 and IL-6 by peritoneal macrophages and fused alveolar macrophages, the cells were collected and cultured as described above. Prior to perform the release, the cells were washed twice with warm MEME and subsequently incubated for 24 hours in 1 ml of MEME supplemented with 5% of HS or FCS, with or without agonist. At the termination of the release, the supernatant were collected, spun at 400 g for 10 minutes, transferred to microfuge tubes and stored at −20° C. until assayed. Macrophages remained adherent and viable in all experiments as determined by DNA measurements and trypan blue exclusion.

IL-1 Bioassay

IL-1 activity in the macrophage supernatants was measured according to Gillis and Mizel (Proc. Natl. Acad. Sci., USA, 1981, 78:1133–1137). LBRM-33 cells, clones 1A5 and 5A4 (ATCC, Rockville, Md.) were stimulated with either PHA (Gibco), rm IL-1β or $log_2$ dilutions of the macrophage supernatants. LBRM-33 lymphocyte supernatants were harvested from 24 hour cultures and subsequently tested for IL-2 activity using a standard microassay, Gillis et al. (J. Immunol., 1978, 120:2027–2032), based on the IL-2 dependent exponential proliferation of a murine cytotoxic T-cell line CTLL (ATCC, Rockville, Md.), Gillis and Smith (Nature (London), 1977, 268:154–156). CTLL cells were cultured in the presence of a $\log_2$ dilution series of putative IL-2 containing samples. After 24 hours, the cells were exposed to 0.5 $\mu$Ci[$^3$H]dThd (20 mCi/mmol, New England Nuclear) for an additional 4 hours after which the cultures were harvested onto glass fiber filter strips with the aid of a multiple automated sample harvester (MASH 11, Microbiological Associates, Bethesda, Md.) [$^3$H]dThd incorporation was determined by direct counting.

IL-6 Bioassay

Five thousand,B13.29 cells subclone B9 (donated by Dr. Thomas Kupper, Washington University of School of Medicine, Washington, Mo.) were cultured in the presence of a $\log_2$ dilution series of macrophage supernatants or standard dilutions of rmIL-6 according to Aarden, L. A. ( Eur. J. Immunol., 1987, 17:1411–1416). Cells were labeled after 24 hours for 1 hour with 0.2 $\mu$Ci [$^3$H]dThd (20 mCi/mmol, New England Nuclear).

Generation of Intracellular cAMP

For cAMP studies, cells were grown under the conditions described above but using either 24 or 96 well dishes. Each well contained either $2\times10^5$ or $5\times10^4$ cells grown in 800 or 200 $\mu$l, respectively. The cells were first washed with warm MEME and subsequently incubated at 37° C. in MEME supplemented with BSA (1 mg/ml) (Sigma Chemical, St. Louis, Mo.) either in the absence or presence of Salmon Calcitonin (sCT) (kindly provided by Dr. Orlowski, Rorer Central Research, Horsham, Pa.), rat calcitonin gene-related peptide (CGRP) (Bachem, Inc., Torrance, Calif.) and 3-isobutyl-1-methylxanthine (IBMX)(Sigma) for the indicated times. Incubations were terminated by aspirating the medium and adding 100 $\mu$l of 0.4% perchloric acid to each well. Perchloric acid extracts were neutralized with 1.5M KOH and stored at −20° C. These samples were acetylated and cAMP measured by radioimmunoassay using succinylated $^{125}$I-labeled cARP (Biomedical Technologies, Inc., Stoughton, Ma.). Results were expressed as fentomoles of CAMP per well. Experiments were performed in duplicates or triplicates and repeated at least 3 times.

DNA Measurements

DNA was measured using a modification of the technique described by Labarca and Paigen (Anal. Biochem., 1980, 102:344). In brief, plated cells were quickly rinsed with PBS prior to a 20-minute incubation at 37° C. in 200 $\mu$l of 10 mM EDTA pH 12.3. The cells were then cooled on ice and adjusted to pH 7.0 by the addition of 12 $\mu$l of 2 mM $KH_2PO_4$. Each cell lysate was then added to 1.8 ml of TES buffer (10 mM TRIS-HCl, 100 mM NaCl, pH 7.0) containing 400 ng/ml of Hoechst dye (H 33258, Boehringer Mannheim, Germany). DNA was quantitated by measuring fluorescence on the Perkin-Elmer LS-5 fluorimeter (Excitation=330; Emission=455). Phenol extracted calf thymus DNA was used as a standard.

Reagents 1,25(OH)$_2$-vitamin $D_3$ was a gift of Dr. Uskokkovic (Hoffman-La Roche, Nutley, N.J.). Salmon Calcitonin (Conn.) was kindly provided by Dr. Orlowski (Rorer Central Research, Horsham, Pa.). Rat Calcitonin Gene-Related Peptide (CGRP) was purchased from Bachem, Inc. (Torrance, Calif.), and Forskolin from Calbiochem (La Jolla, Calif.). Recombinant Murine Interferon-γ (rMuIFNγ) (specific activity $6.8\times10^6$ units/mg) was prepared at Genentech, Inc. (South San Francisco, Calif.), stored at 4° C. in concentrated form and diluted immediately prior to use. The activity of rMuIFNγ was determined by a cytopathic effect inhibition assay using L929 murine fibroblasts challenged with encephalomyocarditis virus. This preparation contained 0.034 EU/mg by the limulus amoebocyte lysate test where 1 EU is the amount of limulus amoebocyte lysate-reactive material of US pharmacopeia reference standard endotoxin. The rabbit polyclonal antisera directed against rMuIFNγ (neutralization titer=$5\times10^4$ U/mg) was also prepared at Genentech, Inc.

Recombinant murine interleukin-1β and a rabbit antibody directed against interleukin-1β were provided by Dr. R. C. Newton (Dupont, Glenolden, Pa.). A mAb directed against murine interleukin-1α ( (mAb 161.1) was a gift of Dr. David Chaplin (Washington University School of Medicine, Washington, Mo.). IL-2, IL-6, anti-IL-6, recombinant human interleukin-2 and -6, and a polyclonal rabbit antiserum were purchased from Genzyme (Boston, Ma.). A polyclonal rabbit antiserum anti-CGRP was provided by Dr. Susan Amara.

RESULTS

Giant Cell Formation in vitro

The fusion of rat macrophages is easily induced in vitro by plating alveolar macrophages at maximal density, i.e., cell-cell contact, and culturing them for 3 to 4 days in medium supplemented with 5% human serum. When peritoneal macrophages from the same animals are grown in these conditions, they remain mononucleated and can therefore be used as a nonfusing control population. It was previously confirmed that giant cells differentiate in vitro by actual cell-cell fusion since DNA synthesis cannot be detected and that the total amount of DNA remains constant during culture in both alveolar and peritoneal macrophages. Therefore, the actual number of alveolar macrophages is decreased drastically by day 4 when each giant cell contains hundreds of nuclei. The important point is that the total number of nuclei remains constant so that we refer to giant cells and peritoneal macrophages as such or else as number of plated cells.

CGRP Inhibition of IL-1 Release

Inflammatory reactions are initiated in part by macrophages which secrete factors that activate lymphocytes in response to activation by bacterial infection and local stimuli. While IL-6 appears to be released by macrophages in the absence of stimulus, IL-1 secretion requires prior activation of the macrophages. Because of their apparent different regulatory mechanism and yet their critical role in immune reactions, these two cytokines were selected to investigate the putative role of calcitonin in multinucleated macrophage functional regulation.

Using a highly sensitive bioassay to measure IL-1 activity, detection of IL-1 activity was first attempted in the macrophage supernatants. IL-1 activity was very elevated (20 pg ±5.0 per $10^6$ plated cells, n =3) in the first 24-hour macrophages release media, i.e., following isolation and plating of the cells, most likely in response to mechanical stimuli and new environment. By day 3, both peritoneal and fused alveolar macrophage supernatants contained a 20-fold lower concentration of IL-1 activity. The addition of salmon calcitonin (sCT) to the release medium on day 3 reduced significantly the amount of IL-1 activity detected in giant cell supernatants but not in peritoneal macrophages. To verify the specificity of calcitonin effect, the macrophages from adjacent wells were treated with calcitonin gene-related peptide (CGRP), a neuropeptide encoded by the same gene as calcitonin. Surprisingly, CGRP prevented the release of IL-1 by both cell types. Because both CT and CGRP evoke a cAMP response in osteoclasts and muscle cells, respectively, whether this nucleotide was the second messenger involved in the regulation of IL-1 secretion was investigated. The addition of forskolin (a potent activator of adenylyl cyclase) to the release medium, was as effective as CGRP in blocking the secretion of IL-1 by both cell types. These biological activities were also blocked when the cell super-natants were preincubated with antibodies directed against IL-1β and IL-1α, thus demonstrating that IL-1β and IL-1αwere responsible for the activity detected in this bioassay.

Simultaneously, both macrophage supernatants demonstrated significant IL-6 activity which level remained identical on day one and 3 ($0.4\pm0.1$ fg per $10^6$ plated cell per day). Of interest is the fact that neither sCT nor CGRP treatment of the cells modified this level.

Therefore, although both IL-1 and IL-6 appear to be constitutively released by macrophages cultured in these conditions, the regulation of their secretion is governed by different extra cellular factors. Of importance is the fact CGRP obviated IL-1 release from both cell types while CT effects were restricted to giant cells. These results suggest that peritoneal macrophages and giant cells differ functionally and that CT and CGRP may bind to different receptors.

Because 1,25(OH)$_2$-vitamin D$_3$ has been shown to stimulate osteoclastic bone resorption and IL-1 release from macrophages, it was deemed critical to verify whether macrophages cultured in these conditions responded to these hormones and cytokine. As expected, the addition of 1,25 (OH)$_2$-vitamin D$_3$ stimulated the proliferation of CTLL cells, and probably IL-1 release but only by peritoneal macrophages. Therefore, these data not only confirm earlier reports on mononucleated macrophages but also demonstrate that giant cells fail to respond to 1,25(OH)$_2$-vitamin D$_3$, therefore providing further evidence that multinucleation modifies the immunological role played by macrophages.

To further investigate the molecular interactions controlling macrophage function, tests were next conducted to determine if CGRP could inhibit vitamin D$_3$ stimulated peritoneal macrophages. It was determined that, although to a lesser extent, CGRP was able to reduce significantly the IL-1 bioactivity present in peritoneal macrophage supernatants.

This inhibitory activity is not reversed by the immunoprecipitation of CGRP with an antibody anti-CGRP from the macrophage supernatants prior to testing in the IL-1 bioassay. Thus confirming that CGRP prevents directly IL-1 release by macrophages.

However, the addition of CGRP to IL-1 containing medium prevents the proliferative response of CTLL cytotoxic T cells in the IL-1 bioassay. This suggests that CGRP either inhibits IL-2 (and/or IL-4) production by proliferation. Because the treatment of the CTLL cells directly with CGRP, in the presence of IL-2, did not prevent significantly their proliferation, we conclude that CGRP prevents IL-2, and/or IL-4 and/or other cytokine secretion by LBRM-33 cells. Thus, CGRP suppresses the immune response at multiple levels by binding to macrophages and lymphocytes and modifying their function.

Taken together, these results suggest that giant cells release cytokines and that the neuropeptide CGRP directly prevents IL-1 and/or IL-2 (IL-4) release by giant cells, macrophages or lymphocytes. Moreover, the above results suggest that IL-1 secretion and/or IL-2/IL-4 inhibition is mediated by cAMP. To further investigate the mechanism by which CT and CGRP inhibits IL-1 secretion, their effect on cAMP production in peritoneal macrophages and giant cells was first investigated.

CGRP stimulates CAMP Production in Peritoneal Macrophages and Giant Cells but CT Effects are Restricted to Giant Cells Both CT and CGRP evoke a cAMP response in osteoclasts and muscle cells, respectively. To detect a putative accumulation of cAMP in giant cells and peritoneal macrophages in response to sCT, peritoneal macrophages and giant cells were incubated for the indicated times in the absence or presence of either salmon calcitonin (sCT), isobutylmethylxanthine (IBMX), or sCT plus IBMX. While sCT failed to induce a response in peritoneal macrophages at all time points examined, a pic of cAMP accumulation was detected as early as 5 minutes after addition of the peptide to fused alveolar macrophages. This lag time was reduced to 2 minutes when as little as 10 $\mu$M IBMX, a phosphodiesterase inhibitor and cAMP returned to basal level after 15 and 30 minutes, in the absence and presence of IBMX, respectively.

Neither MEME alone or with IBMX were able to induce CAMP accumulation.

When the dose response effect of sCT on cAMP production in giant cells was examined, a dose-dependence of sCT was recorded. Half maximal stimulation of cAMP accumulation in giant cells (50 fmoles per $6.4\times10^4$ plated cells) was attained at a concentration of 2 nM.

Therefore, giant cells but not peritoneal macrophages respond to sCT by elevating their concentration of cytoplasmic cAMP, thus corroborating the above results showing that CT inhibition IL-1 release is specific for giant cells. Conversely, when a dose-dependent cAMP accumulation was measured after 2 minutes of incubation with CGRP in the presence of IBMX, both mononucleated and fused macrophages responded. Although fused alveolar macrophages repeatedly accumulated more cAMP than peritoneal macrophages, the half maximal concentration of cAMP (300 vs. 80 fmoles per $5\times10^4$ plated cells, respectively) was also attained by the addition of 2 nM CGRP in both cell types.

To investigate whether this different in amplitude was associated with multinucleation, cAMP accumulation in response to CGRP was recorded as a function of time. This difference was detected as early as 2 hours after plating the cells which both accumulated higher concentrations of cAMP with time in culture to reach a plateau by day 2 (fmoles per $5\times10^4$ cells). Medium alone or supplemented with IBMX was not able at any time point measured to induce a cAMP accumulation in these cells. Of importance is the fact that CGRP induced a larger accumulation of cAMP in macrophages than CT, thus correlating with their respective effects on IL-1-release inhibition. These data are consistent with the proposition that macrophages, whether mono- or multinucleated do express CGRP receptors and that culturing them increases the amplitude of their cAMP response to this neuropeptide. Moreover, these data strongly suggest that cAMP mediates the effects of both CT and CGRP on IL-1 secretion.

A human being suffering from chronic rheumatoid 0 arthritis experiences an amelioration of the symptoms of the disease, e.g., pain and swelling of the affected joints, by the I.M. administration of 0.5 mg of CGRP every 24 hours until relief is noted. Similar results are observed by injection of the CGRP into an affected joint.

Osteoporosis has been recently linked to an abnormally high IL-1 release level. In accordance with this invention, CGRP is more potent than CT in inhibiting the degenerative process of the bone.

Organ transplant is accompanied by an acute inflammatory reaction associated with surgery and a chronic inflammatory reaction associated with graft rejection. In accordance with this invention, CGRP is useful in limiting the rejection process by reducing the inflammatory reaction.

IL-1 is secreted by keratinocytes (skin cells), endothelial cells (vascular wall), mesangial cells (kidney) and glial cells (brain); therefore, clinical applications for the use of CT and CGRP embrace a vast array of diseases involving all tissues and organs, since they are all vascularized, involved in a chronic or acute inflammatory reaction, e.g., in response to injury, surgery, infection or autoimmunity.

For example, CT and CGRP can be used to limit the inflammatory condition associated with surgery, with or without organ transplant, following cancer, trauma, metabolic diseases; orthopedic surgery, following or not trauma and associated with chronic inflammation and non-repair; allergic reactions involving skin (eczema), lung (asthma), eyes, digestive tract, nervous system, etc.

Additionally, because nervous tissue is rich in CGRP receptors and glial cells secrete IL-1, CGRP therefore may be used for treatment of mental problems, headaches and earaches; periodontal disease involves chronic inflammation, which leads to bone destruction and ultimately tooth loss. The use of CT or CGRP as a topical solution limits the course of this disease, as well as limiting gingivitis and periodontitis.

Because ovulation is associated with IL-1 release, inflammation and fever, CGRP can be used as an antipregnancy drug, e.g., as an oral contraceptive.

CGRP, as a potent immunosuppressor, can help facilitate pregnancy or feto-maternal biological interactions (prevent the rejection of the fetus in noncompatibility of blood types) and help to prevent rejection of transplanted/implanted organs.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of down-regulating the immune response via cytokine release and receptor expression by immune and non-immune cells, interleukin-1 (IL-1) release or IL-1 and interleukin-2 (IL-2) release from interleukin-1 and interleukin-2 releasing cells in a living mammal which comprises administering thereto an immunosuppressive amount of calcitonin gene-related peptide (CGRP).

2. A method according to claim 1, wherein the human being is suffering from a hyperimmune response-related disease resulting from the cytokine release and the amount of CGRP administered is effective to ameliorate the disease.

3. A method according to claim 2, wherein the CGRP is administered by injection.

4. A method according to claim 3, wherein the injection is intramuscular.

5. A pharmaceutical composition adapted for noningestion systemic administration which comprises per unit dosage an IL-1 release-inhibiting amount of CGRP in admixture with a pharmaceutically acceptable carrier.

6. A pharmaceutical composition according to claim 5, adapted for injection.

7. A pharmaceutical composition according to claim 6, wherein the admixture is a dry solid which is soluble in water.

* * * * *